(12) United States Patent
Park (10) Patent No.: US 9,348,968 B2
(45) Date of Patent: May 24, 2016

(54) SYSTEM AND METHOD FOR PROCESSING GENOME SEQUENCE IN CONSIDERATION OF SEED LENGTH

(71) Applicant: SAMSUNG SDS CO., LTD., Seoul (KR)

(72) Inventor: Minseo Park, Seoul (KR)

(73) Assignee: SAMSUNG SDS CO., LTD., Seoul (KR)

( * ) Notice: Subject to any disclaimer, the term of this patent is extended or adjusted under 35 U.S.C. 154(b) by 715 days.

(21) Appl. No.: 13/728,116

(22) Filed: Dec. 27, 2012

(65) Prior Publication Data

US 2013/0238250 A1    Sep. 12, 2013

(30) Foreign Application Priority Data

Mar. 6, 2012    (KR) .................. 10-2012-0022647

(51) Int. Cl.
*G06F 19/22*    (2011.01)
*G06F 15/00*    (2006.01)
*G06F 19/10*    (2011.01)

(52) U.S. Cl.
CPC ............... *G06F 19/10* (2013.01); *G06F 19/22* (2013.01)

(58) Field of Classification Search
None
See application file for complete search history.

(56) References Cited

U.S. PATENT DOCUMENTS

2011/0270533 A1    11/2011    Zhang et al.

FOREIGN PATENT DOCUMENTS

JP    2013-172709 A    9/2013

OTHER PUBLICATIONS

Communication dated Dec. 5, 2014 issued by the Japanese Patent Ofice in counterpart Japanese Patent Application No. 2012-227078.
Warren, et al; "Targeted Assembly of Short Sequence Reads"; PLoS ONE/www.plosone.org; vol. 6; iss. 5; May 2011; pp. 1-6; 7 pages total.
Zaharia, et al; "Faster and More Accurate Sequence Alignment with SNAP"; arXiv:1111.5572v1 [cs.DS.]; Nov. 23, 2011; pp. 1-10; 11 pages total.
Kielbasa, et al; "Adaptive seeds tame genomic sequence comparison"; Cold Spring Harbor Laboratory Press; Genome Research; 2011; pp. 487-493; 8 pages total.
Communication, dated Feb. 20, 2014, issued by the European Patent Office in counterpart European Patent Application No. 12187721.1.
Kielbasa, Szymon M., et al., "Adaptive seeds tame genomic sequence comparison," Cold Spring Harbor Laboratory Press, Genome Research, vol. 21, No. 3, Jan. 5, 2011, pp. 487-493.
Csürös, Miklós, "Performing Local Similarity Searches with Variable Length Seeds," Combinatorial Pattern Matching, Lecture Notes in Computer Science vol. 3109, Jan. 1, 2004, pp. 373-387.
Ye, Yuzhen, et al., "RAPSearch: a fast protein similarity search tool for short reads," BMC Bioinformatics, BioMed Central, vol. 12, No. 1, May 15, 2011, pp. 1-10.
Trapnell, et al., "How to map billions of short reads on to genomes", Nature Biotechnology, May 2009, pp. 455-457, vol. 27, No. 5.
Flicek, et al., "Sense from sequence reads: methods for alignment and assembly", Nature Methods Supplement, Nov. 2009, pp. 6-12, vol. 6, No. 11.
Bao, et al., "Seed: efficient clustering of next-generation sequences", Bioinformatics, 2011, pp. 2502-2509, vol. 27., No. 18.
Communication from the Japanese Patent Office dated Apr. 1, 2014, in a counterpart Japanese application No. 2012-227078.

*Primary Examiner* — John S Brusca
(74) *Attorney, Agent, or Firm* — Sughrue Mion, PLLC (57) ABSTRACT

Provided are systems and methods for processing a genome sequence by adjusting seed length. Exemplary systems for processing a genome sequence may include a seed extractor configured to extract a seed from a target sequence; and an index generator configured to index the seed extracted from the seed extractor. In some embodiments, the length of the seed extracted is adjusted based on the number of seeds extracted from the target sequence that have the same nucleotide sequence.

26 Claims, 6 Drawing Sheets

FIG. 1

TARGET SEQUENCE : G T G G C A A T T A A A T C G T T G G ...

SEED
- G T G G C A A T T A
- T G G C A A T T A A
- G G C A A T T A A A
- G C A A T T A A A T
- C A A T T A A A T C
- A A T T A A A T C G
- A T T A A A T C G T
- T T A A A T C G T T
- T A A A T C G T T G
- A A A T C G T T G G

SYSTEM AND METHOD FOR PROCESSING GENOME SEQUENCE IN CONSIDERATION OF SEED LENGTH

CROSS-REFERENCE TO RELATED APPLICATION

This application claims priority from Korean Patent Application No. 10-2012-0022647, filed on Mar. 6, 2012 in the Korean Intellectual Property Office, the disclosure of which is incorporated herein by reference in its entirety.

BACKGROUND

The advent of next generation sequencing (NGS), and the reduction in cost of DNA sequencing, make possible large-scale human genome sequencing for research in medical genetics and population genetics. NGS sequencers used for analyzing genome sequences can produce several billions of very short fragment sequences (referred to as "reads"). The genome sequence of an individual is obtained through resequencing (including indexing, mapping and alignment), and by determining the locations of the generated reads in a whole genome sequence.

Early systems for genome sequencing mainly focused on the accuracy of the sequencing. However, as the use of NGS has become more widespread, the cost of generating each read has significantly dropped, whereas the amount of generated data useful for the sequence analysis has increased. Therefore, there is a need for sequencing technology that can quickly and accurately process high-capacity reads.

SUMMARY

In exemplary embodiments, systems and methods are provided for rapidly and accurately sequencing a whole genome. In some embodiments, the target sequence is a whole genome including read sequences extracted from a sequencer.

According to an aspect of an exemplary embodiment, there is provided a system for processing a genome sequence, which system may include: a seed extractor configured to extract a seed from a whole genome or read sequence; and an index generator configured to index the seed that is extracted from the seed extractor. In some embodiments, the length of the extracted seed may be adjusted based on the number of seeds having the same nucleotide sequence extracted from a whole genome. For example, if the number of seeds extracted from a whole genome or read sequences which have the same nucleotide sequence is determined to be excessive, the seed length may be increased, and vice-versa.

According to an aspect of another exemplary embodiment, there is provided a method for processing a genome sequence, which method may include: extracting a seed from a whole genome or read sequences; and indexing the extracted seed. The length of the extracted seed may be adjusted based on the number of seeds extracted from the target sequence that have the same nucleotide sequence. For example, if the number of seeds extracted from the target sequence which have the same nucleotide sequence is determined to be excessive, the seed length may be increased, and vice-versa.

According to an aspect of another exemplary embodiment, there is provided a method of processing a base sequence, the method including extracting a seed from the target sequence. In some embodiments thereof the target sequence is a whole genome including read sequences extracted from a sequencer. The length of the extracted seed may be adjusted based on the number of seeds extracted from the target sequence that have the same nucleotide sequence. For example, if the number of seeds extracted from the target sequence which have the same nucleotide sequence is determined to be excessive, the seed length may be increased, and vice-versa.

BRIEF DESCRIPTION OF THE DRAWINGS

The above and other objects, features and advantages will become more apparent to those of ordinary skill in the art by describing in detail exemplary embodiments with reference to the attached drawings, in which.

DETAILED DESCRIPTION OF EXEMPLARY EMBODIMENTS

Hereinafter, exemplary embodiments will be described in detail. However, it is understood that all exemplary embodiments are not limited to exemplary embodiments disclosed below, but can be implemented in various forms. The following exemplary embodiments are described in order to enable those of ordinary skill in the art to embody and practice exemplary embodiments.

Although the terms first, second, etc. may be used to describe various elements, these elements are not limited in their order of appearance or operation by these terms. These terms are only used as expedients to connote the existence of different elements. For example, a first element could be termed a second element, and, similarly, a second element could be termed a first element. The term "and/or" includes any and all combinations of one or more of the associated listed items.

When an element is "connected" or "coupled" to another element, it may be directly connected or coupled to the other element, or one or more intervening elements may be present. In contrast, when an element is referred to as being "directly connected" or "directly coupled" to another element, there are no intervening elements present.

The terminology used herein is for the purpose of describing particular exemplary embodiments only and is not intended to be limiting of exemplary embodiments. The terms "a," "an" and "the" encompass both singular and plural forms, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments will be described in greater detail below. To aid understanding, like numbers refer to like elements throughout the description of the figures, and the description of the same elements will not be reiterated.

The term "read" is a fragment of a genome sequence that is sequenced and outputted from a genome sequencer. The length of a particular read may vary, and in some embodiments, may be about 35 to 500 base pairs (bp) in length. As those skilled in the art would appreciate, the length of read varies depending on the type of genome sequencing technology employed. DNA bases are generally denoted using the letters A, C, G and T.

The term "target sequence" refers to a reference sequence. A complete genome sequence may be assembled by mapping a large number of reads outputted from a genome sequencer onto a reference. In some embodiments, the target sequence may be a predetermined reference sequence (e.g., a complete genome sequence of a human) in the analysis of a genome sequence. In other embodiments, a genome sequence generated by a genome sequencer can also be used as the target sequence.

Target sequences and reads constitute sequences of bases, with bases in DNA being commonly designated as A, C, G or T, depending on the chemical structure of the base. However, for various reasons (e.g., a sequencing error, a sampling error, etc.), a target sequence may contain one or more bases that are of uncertain identity. Such bases are generally denoted as a separate letter, such as "N."

The term "seed" is a unit sequence used for mapping reads onto a target sequence. Theoretically, when mapping reads onto a target sequence, all the reads should be sequentially compared with the target sequence, beginning with the first part thereof, in order to estimate the positions in the target sequence from which each read is produced. However, one disadvantage of this approach is that it requires excessive time and computing resources to map a read. For this reason, in practice, a hash table is constructed by hashing a predetermined length of the target sequence, beginning with the first part thereof, and advancing one base at a time, and then the read is mapped to a position on the target sequence. In some embodiments, the fragment of the target sequence for hashing becomes a seed. However, in other embodiments, a fragment of the read may be a seed. In exemplary embodiments, the seed length may be smaller than the length of the read(s), and the seed length may also be adjusted depending on the length of the target sequence, and/or the capacity of the constructed hash table.

Figure 1:
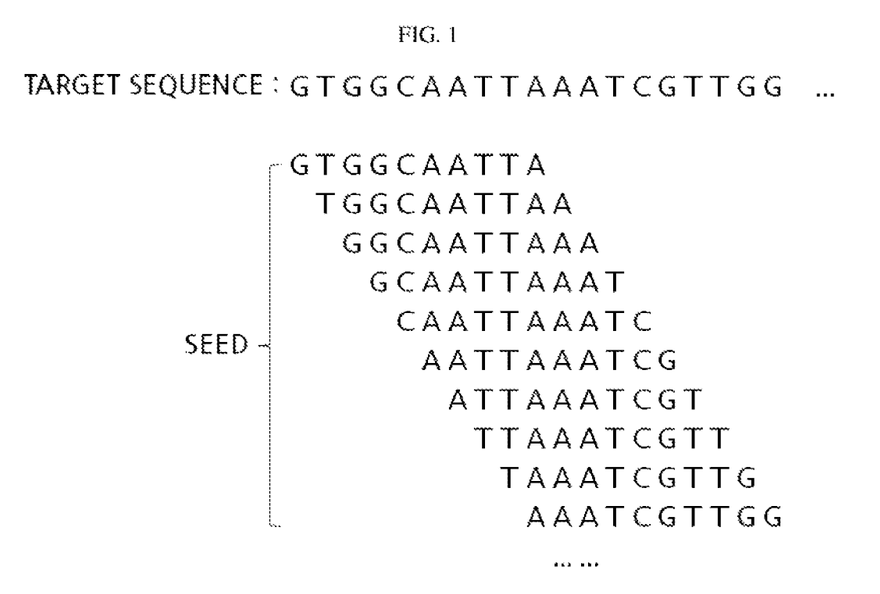
FIG. 1 is a diagram illustrating an example of extraction of a plurality of seeds (depicted, from top to bottom, by SEQ ID NOs: 3-12) from a target sequence (SEQ ID NO: 1)

FIG. 1 illustrates an example of extraction of a seed from a target sequence. In the example, the seed is extracted by extracting the base sequence of the target sequence one base at a time in a length of 10 bp from the first part thereof. All the extracted seeds have the same length (10 bps in the example shown in FIG. 1), but the sequences of the seeds are different from one another depending on the positions of the bases extracted from the target sequence. In the example shown in FIG. 1, the first extracted seed contains the $1^{st}$ to $10^{th}$ bases of the target sequence, which is G T G G C A A T T A (SEQ ID NO: 3), and the third extracted seed has the $3^{rd}$ to $12^{th}$ bases of the target sequence, which is G G C A A T T A A A (SEQ ID NO: 5).

Figure 2:
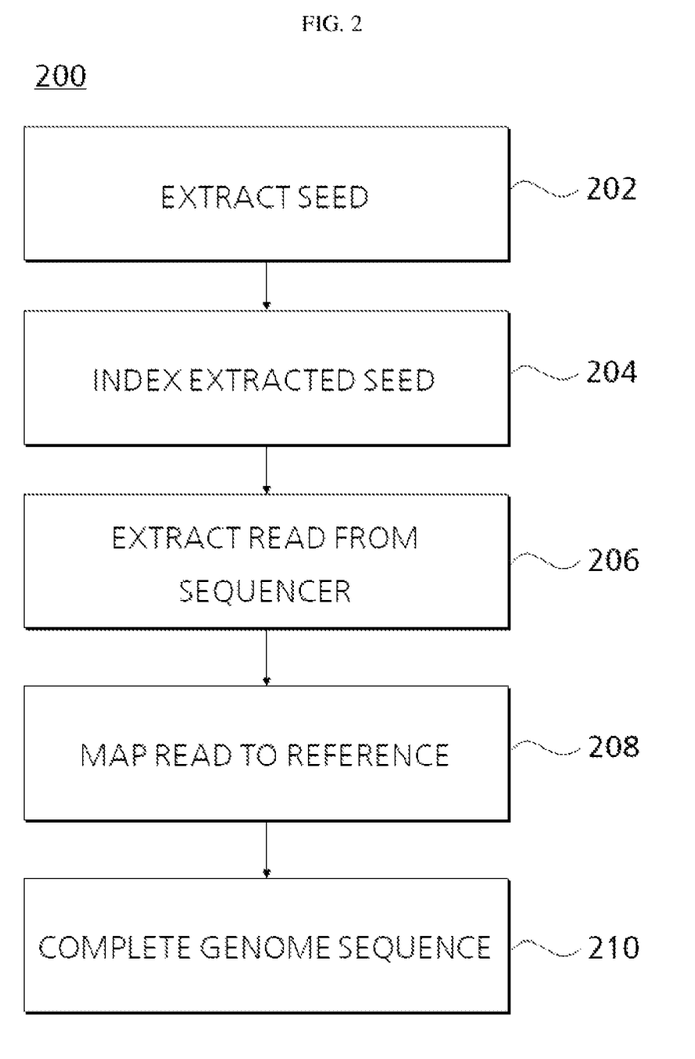
FIG. 2 is a flowchart illustrating an example of genome sequencing.

FIG. 2 is a flowchart illustrating an exemplary method for genome sequencing (S200). It allows the assembly of a complete genome sequence by mapping a large quantity of short reads outputted from a genome sequencer onto a target sequence.

First, a seed is extracted from a target sequence (S202). In the exemplary embodiment shown in FIG. 1, a plurality of seeds are extracted by sequentially extracting sequences of bases of a predetermined length from the target sequence, beginning with the first part thereof, and advancing one base at a time.

Subsequently, the seeds extracted in S202 are hashed using a predetermined hash function, and thereby a hash table is produced (S204). The hash table may be keyed with a value generated from the seed. In some embodiments, the value indicates the location in the target sequence to which the seed corresponds.

Then, a plurality of reads is extracted from the genome sequencer (S206), and the extracted reads are mapped onto the target sequence using the hash table (S208).

Figure 3:
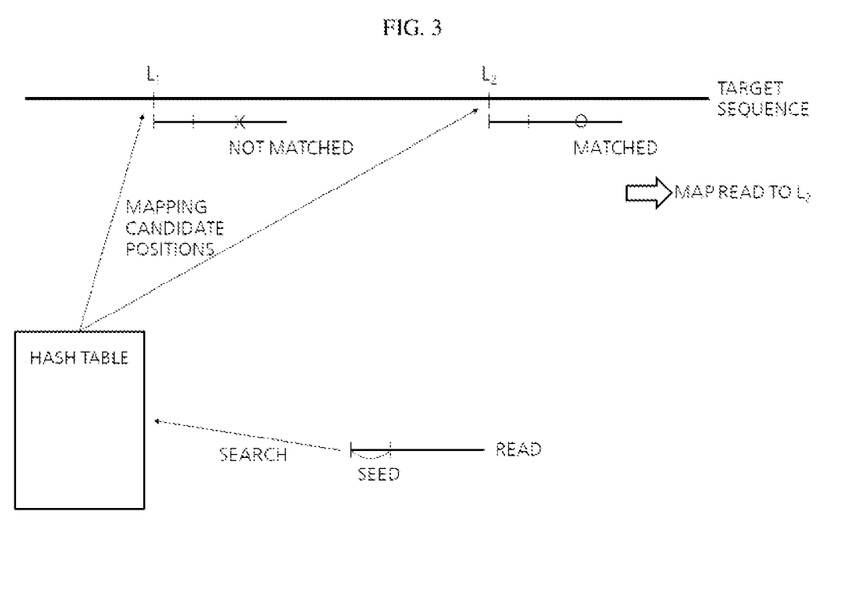
FIG. 3 is a diagram illustrating an example of mapping reads onto a target sequence during genome sequencing.

FIG. 3 is a diagram illustrating an example of the mapping of reads onto a target sequence, in the manner described above. First, the N by (N is a seed length) of the read extracted in S206 is read out as a seed, and one or more mapping candidate positions of the seed in the target sequence are obtained by searching the hash table. In this example, the first part of the read is used as a seed, but in practice, the seed may be any part of the read. However, because the accuracy of the first part of the read is generally high, in some embodiments, the first part of the read is used as a seed. In this case, at least one mapping candidate position is generally obtained (In Table 3, two mapping candidates $L_1$ and $L_2$ are obtained). The number of mapping candidate positions vary depending on seed length.

Subsequently, the remaining part of the read is compared with the target sequence at each of the mapping candidate positions, to determine an exact mapping position of the read. In the illustrated example, at $L_1$, the read does not correspond to the target sequence, but the read corresponds to the target sequence at $L_2$. As a result, the read is mapped to the $L_2$ position.

The reads mapped through the above-described exemplary process are then connected to each other, thereby assembling the genome sequence (S210).

Figure 4:
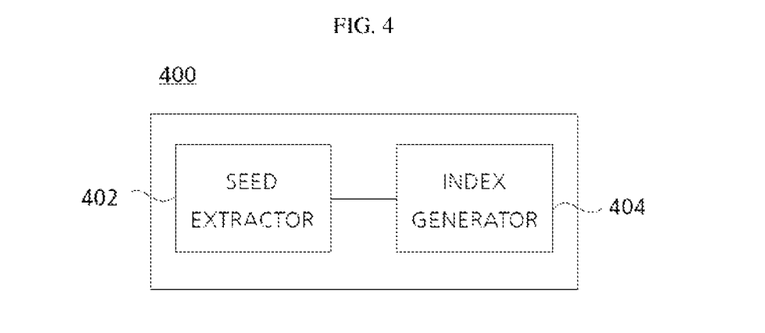
FIG. 4 is a block diagram of an exemplary system for processing a genome sequence.

FIG. 4 is a block diagram of an exemplary system for processing a genome sequence 400. In this exemplary system, the system for processing a base sequence 400 may be configured as a separate system, or alternatively, may be included as one element in the system for analyzing a genome sequence.

As shown in FIG. 4, an exemplary system for processing a genome sequence 400 includes a seed extractor 402 and an index generator 404.

The seed extractor 402 extracts a seed from a target sequence. The target sequence may be a complete genome sequence to be analyzed, that is, a reference sequence. However, the target sequence of the present invention is not so limited, and may be, for example, the read extracted from the sequencer. The target sequence of the present invention includes any kind of genome sequence from which a seed can be extracted.

The seed extractor 402 may be configured to extract a plurality of seeds by sequentially extracting sequences of bases of a predetermined length from the target sequence, beginning with the first part thereof, and advancing one base at a time. The length of the extracted seed may be adjusted based on the number of seeds extracted from the target sequence that have the same nucleotide sequence. For example, if the number of seeds extracted from the target sequence which have the same nucleotide sequence is considered excessive, the seed length may be increased, and vice-versa.

The index generator 404 indexes the seed extracted from the seed extractor 402. Specifically, the index generator 404 is configured to index the seed by hashing the seed extracted from the seed extractor 402 using a hash function, and generating a hash table using the hashed seed as a key.

Hereinafter, an exemplary procedure for determining a seed length to be used by the seed extractor 402 will be described.

To increase the accuracy of the genome sequencing generated by processing the reads, in some embodiments, the reads outputted from the genome sequencer should be uniformly distributed along the target sequence. To this end, it may be desirable to reduce duplication of the seeds (i.e., reduce the number of seeds having the same sequence). The following exemplary target sequence is presented for illustration purposes only.

(SEQ ID NO: 2)
ACTCTGGTGCATACCTCCTGGCTGGACTCTGG

When a seed having a length of 6 bp is extracted from this target sequence, ACTCTG and CTCTGG are duplicated twice. When the seed length is 3 bp, a seed having a sequence of TGC is duplicated five times. That is, as the seed length is decreased, the number of duplicated seeds increases, and therefore the number of candidate positions in the target sequence onto which reads must be mapped also increases. For example, when the upstream region of the read extracted in this exemplary embodiment has a length of 3 bp and starts with TGC, the corresponding read needs to be compared to a total of 5 candidate positions. For this reason, the mapping time is increased, while the accuracy of the mapping is decreased.

Provided that a seed length is S and the number of bases constituting the target sequence is B, seeds capable of being generated according to the seed length are determined using the following Equation:

$$\text{Cases of seeds capable of being generated} = B^S \quad \text{[Equation 1]}$$

In Equation 1, if a target sequence consists of four bases, A, C, G and T, B=4, and when an uncertain base (N) is also included, B=5.

Provided that the length of a complete target sequence for extracting a seed is R (when the target sequence is a human base sequence, R is approximately $3 \times 10^9$), an average number of seeds having the same sequence throughout the complete target sequence (a quantity of duplicated seeds) may be determined as follows:

$$\text{Number of duplicated seeds} = R/B^S \quad \text{[Equation 2]}$$

Table 1 shows an average number of duplicated seeds per seed length in a human genome.

TABLE 1

| Seed Length | 13 | 14 | 15 | 16 |
|---|---|---|---|---|
| Number of Duplicated Seeds | 44.70 | 11.18 | 2.79 | 0.70 |

Provided that a target value (or set value) of a number of duplicated seeds among the seeds extracted from the target sequence is k, then k should satisfy the following Equation. In other words, an average value of a number of the duplicated seeds should be within the target value.

$$0 < R/B^S < k \quad \text{[Equation 3]}$$

Eventually, the seed length is expressed as the following Equation:

$$S > \log_{k \cdot B} R \quad \text{[Equation 4]}$$

In Equation 4, k may in some embodiments be 3 or less, and may be 2 or 3. As the k value decreases (that is, the number of duplicated seeds decreases), the number of mapping candidate positions also decreases. Hence, the speed and accuracy of the mapping are increased. However, when the seed length is excessively short according to the k value, for example due to the presence of a read not being completely matched with the seed, mapping becomes difficult or the size of the hash table becomes excessively large. In some embodiments, the k value may be adjusted depending on such factors.

Figure 5:
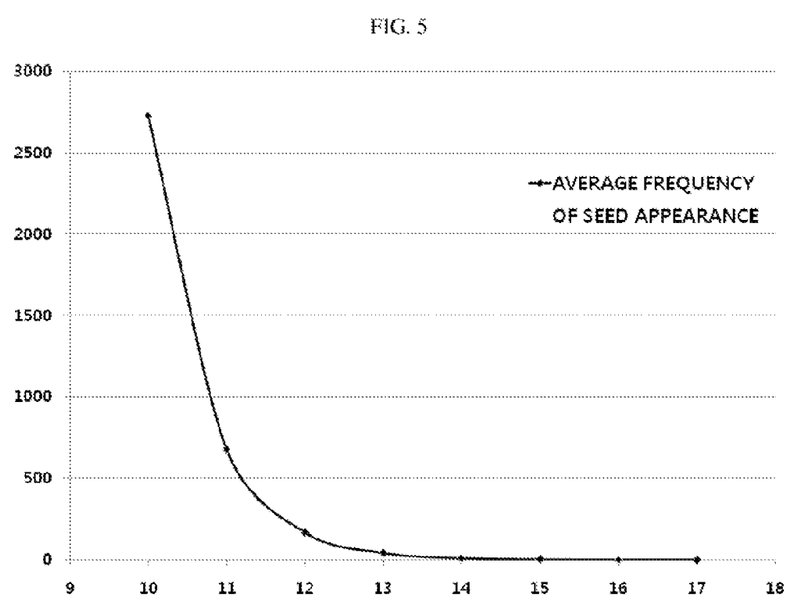
FIG. 5 is a graph showing average frequencies with which seeds of a particular length appear during human genome sequencing.

When the target sequence is a human genome sequence, the seed length (S) in some embodiments may be 15 or more according to Equation 4. Table 2 shows average frequencies of seed appearance in a human genome according to seed length, and FIG. 5 is a graph thereof.

TABLE 2

| Seed Length | Average Frequency of Seed Appearance |
|---|---|
| 10 | 2,726.1919 |
| 11 | 681.9731 |
| 12 | 170.9185 |
| 13 | 42.7099 |
| 14 | 10.6470 |
| 15 | 2.6617 |
| 16 | 0.6654 |
| 17 | 0.1664 |

As can be seen from Table 2, when the seed length is 14 or less, the frequency per seed is 10 or more, and when the seed length is 15 bp, the frequency per seed is decreased to 3 or less. That is, when the seed length is 15 bp, compared with when the seed length is 14 bp or less, the duplication of seeds may be drastically reduced.

In exemplary embodiments, the seed length may be adjusted based on the capacity of an index generated by the index generator 404, and based on the memory capacity of the system for processing a base sequence 100. The longer the seed length, the larger the capacity of a hash table generated therefrom. Accordingly, in some circumstances, the capacity of the hash table may exceed the capacity of memory included in the system for processing a base sequence 100. Therefore, in some embodiments for determining seed length, the above capacities are accounted for. For example, when the target sequence is a human genome sequence, in some embodiments which take into account the capacity of the index and the memory capacity (e.g., the capacity of memory of a single node), the seed length may be 30 bp or less.

Figure 6:
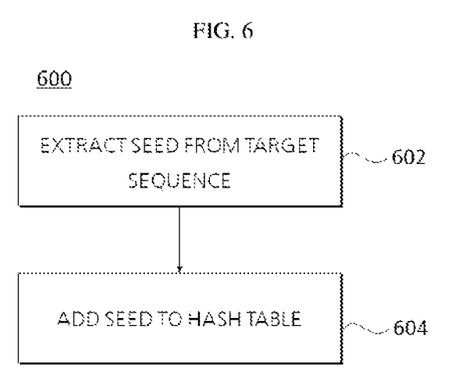
FIG. 6 is a flowchart illustrating an exemplary method for processing a genome sequence.

FIG. 6 is a flowchart of an exemplary method of processing a target sequence (S600).

First, a seed is extracted from a target sequence (S602). In this example, a plurality of seeds are extracted by sequentially extracting sequences of bases of a predetermined length from the target sequence, beginning with the first part thereof, and advancing one base at a time. The length of the extracted seed may be adjusted based on the number of seeds extracted from the target sequence that have the same nucleotide sequence. For example, if the number of seeds extracted from the target sequence which have the same nucleotide sequence is determined to be excessive, the seed length may be increased, and vice-versa. Considerations for determining seed length have been described heretofore, and are thus not reiterated.

Subsequently, the seed extracted in S602 is indexed (S604). Specifically, in this step, the extracted seed is hashed using a hash function, and then the seed is indexed by generating a hash table using a hashed seed as a key.

In other embodiments, a computer-readable recording medium is provided which includes a program for performing methods described herein on a computer. The computer-readable recording medium may include a program command, a local data file, and a local data structure, used alone or in combination. The medium may be specially designed or configured for the present invention, or known to those of ordinary skill in the field of computer software. Examples of the computer-readable recording medium include magnetic media such as a hard disk, a floppy disk and a magnetic tape, optical recording media such as a CD-ROM and a DVD, a magnetic-optical medium such as a floppy disk, and hardware devices specially configured to store and perform program commands such as ROM, RAM and flash memory. The program commands may include a high-level language code capable of being executed by a computer using an interpreter, as well as machine language code, which is, for example, made by a compiler.

Thus, in exemplary embodiments, the length of a seed extracted in a process for sequencing a base sequence is adjusted to provide for improvements in the speed and accuracy of genome sequencing.

What is claimed is:

1. An apparatus for processing a genome sequence, comprising:
   at least one hardware processor;
   computer-readable memory, said memory comprising one or more programs, executed by the at least one hardware processor, which comprise commands for:
   extracting seeds, having a specified seed length, from a target sequence;
   determining the number of extracted seeds that have the same nucleotide sequence, and adjusting the seed length of the extracted seeds based on the number of extracted seeds having the same nucleotide sequence; and
   adding seeds having the adjusted seed length to an index.

2. The apparatus of claim 1, wherein the apparatus adjusts the length of the seed so that the frequency of seeds extracted from said target sequence that have the same nucleotide sequence is not more than a predetermined value.

3. The apparatus of claim 1, wherein the length of the seed is adjusted according to the following Equation:

$$S > \log_{k \cdot B} R$$

where S is the length of the seed, R is the length of the target sequence, B is the number of bases constituting the target sequence, and k is a set value for the frequency of seeds extracted from said target sequence that have the same nucleotide sequence.

4. The apparatus of claim 3, wherein k is 3 or less.

5. The apparatus of claim 1, wherein when the target sequence is a human genome sequence, the length of the seed is adjusted to 15 bp or more.

6. The apparatus of claim 1, wherein said apparatus comprises memory for processing said genome sequence, and wherein the length of the seed is further adjusted based on the capacity of the index, the capacity of the memory for processing said genome sequence, or both.

7. The apparatus of claim 1, wherein when the target sequence is a human genome sequence, the length of the seed is adjusted to 30 bp or less.

8. The apparatus of claim 1, wherein said apparatus is configured to receive reads outputted from a genome sequencer.

9. A method for processing a base sequence, comprising:
   extracting seeds, having a specified seed length, from a target sequence;
   determining the number of extracted seeds that have the same nucleotide sequence, and adjusting the seed length of the extracted seeds based on the number of extracted seeds having the same nucleotide sequence; and
   adding seeds having the adjusted seed length to an index,
   wherein said extracting, said determining, said adjusting, and said adding, are performed using the apparatus of claim 1.

10. The method of claim 9, wherein the length of the seed extracted is adjusted so that the frequency of seeds extracted from said target sequence that have the same nucleotide sequence is not more than a predetermined value.

11. The method of claim 9, wherein the length of the seed is adjusted according to the following Equation:

$$S > \log_{k \cdot B} R$$

where S is the length of the seed, R is the length of the target sequence, B is the number of bases constituting the target sequence, and k is a set value for the frequency of seeds extracted from said target sequence that have the same nucleotide sequence.

12. The method of claim 11, wherein k is 3 or less.

13. The method of claim 9, wherein when the target sequence is a human genome sequence, the length of the seed is adjusted to 15 bp or more.

14. The method of claim 9, wherein the length of the seed is further adjusted based on the capacity of the index generated by said index generator, the capacity of said memory, or both.

15. The method of claim 9, wherein when the target sequence is a human genome sequence, the length of the seed is adjusted to 30 bp or less.

16. A method of processing a genome sequence, comprising:
   extracting seeds, having a specified seed length, from a target sequence;
   determining the number of extracted seeds that have the same nucleotide sequence, and adjusting the seed length of the extracted seeds based on the number of extracted seeds having the same nucleotide sequence; and
   adding seeds having the adjusted seed length to an index,
   wherein said extracting, said determining, said adjusting, and said adding, are performed using the apparatus of claim 1.

17. The method of claim 16, wherein when the target sequence is a human genome sequence, the length of the seed is adjusted to 15 bp or more.

18. The apparatus of claim 1, wherein said one or more programs further comprise commands for hashing seeds which have the adjusted seed length; and commands for generating a hash table using the hashed seeds as keys.

19. The apparatus of claim 1, wherein the seeds are extracted from the target sequence by sequentially extracting sequences of bases of a predetermined length from the target sequence.

20. The apparatus of claim 1, wherein said one or more programs further comprise commands for keying the hash table with a value indicating the location in the genome sequence that each seed corresponds to.

21. The method of claim 9, wherein said method further comprises hashing seeds which have the adjusted seed length; and generating a hash table using the hashed seeds as keys.

22. The method of claim 9, wherein the seeds are extracted by sequentially extracting sequences of bases of a predetermined length from the target sequence.

23. The method of claim 9, wherein said method further comprises keying the hash table with a value indicating the location in the base sequence that the seed corresponds to.

24. The method of claim 16, wherein said method further comprises hashing seeds which have the adjusted seed length; and generating a hash table using the hashed seeds as keys.

25. The method of claim 16, wherein the seeds are extracted by sequentially extracting sequences of bases of a predetermined length from the target sequence.

26. The method of claim 16, wherein said method further comprises keying the hash table with a value indicating the location in the genome sequence that the seed corresponds to.

* * * * *

SEQUENCE LISTING

```
<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 1
gtggcaatta aatcgttgg                                                        19

<210> SEQ ID NO 2
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 2
actctggtgc atacctcctg gctggactct gg                                         32

<210> SEQ ID NO 3
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 3
gtggcaatta                                                                  10

<210> SEQ ID NO 4
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 4
tggcaattaa                                                                  10

<210> SEQ ID NO 5
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 5
ggcaattaaa                                                                  10
```

```
<210> SEQ ID NO 6
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 6
gcaattaaat                                                                 10

<210> SEQ ID NO 7
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 7
caattaaatc                                                                 10

<210> SEQ ID NO 8
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 8
aattaaatcg                                                                 10

<210> SEQ ID NO 9
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 9
attaaatcgt                                                                 10

<210> SEQ ID NO 10
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 10
ttaaatcgtt                                                                 10

<210> SEQ ID NO 11
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 11
taaatcgttg                                                                 10

<210> SEQ ID NO 12
<211> LENGTH: 10
<212> TYPE: DNA
<213> ORGANISM: Artificial Sequence
```

-continued

```
<220> FEATURE:
<223> OTHER INFORMATION: Synthetic polynucleotide

<400> SEQUENCE: 12
aaatcgttgg                                                          10
```